United States Patent
Buelow et al.

(10) Patent No.: US 8,600,133 B2
(45) Date of Patent: Dec. 3, 2013

(54) SELECTION OF SNAPSHOTS OF A MEDICAL IMAGE SEQUENCE

(75) Inventors: Thomas Buelow, Grosshansdorf (DE); Martin Bergtholdt, Hamburg (DE); Lina Arbash Meinel, Homewood, IL (US)

(73) Assignee: Koninklijke Philips N.V., Eindhoven (NL)

( * ) Notice: Subject to any disclaimer, the term of this patent is extended or adjusted under 35 U.S.C. 154(b) by 315 days.

(21) Appl. No.: 13/119,738

(22) PCT Filed: Sep. 23, 2009

(86) PCT No.: PCT/IB2009/054161
§ 371 (c)(1),
(2), (4) Date: Mar. 18, 2011

(87) PCT Pub. No.: WO2010/038172
PCT Pub. Date: Apr. 8, 2010

(65) Prior Publication Data
US 2011/0170755 A1 Jul. 14, 2011

Related U.S. Application Data

(60) Provisional application No. 61/101,691, filed on Oct. 1, 2008.

(51) Int. Cl.
*G06K 9/00* (2006.01)
(52) U.S. Cl.
USPC ........................................................ 382/128
(58) Field of Classification Search
USPC ............. 382/128; 702/39, 159, 171; 433/119; 348/77
See application file for complete search history.

(56) References Cited

U.S. PATENT DOCUMENTS

| | | | |
|---|---|---|---|
| 6,208,353 B1 | 3/2001 | Ayer et al. | |
| 7,865,230 B1 * | 1/2011 | Sevick-Muraca et al. | 600/473 |
| 2004/0101181 A1 * | 5/2004 | Giger et al. | 382/128 |
| 2005/0096530 A1 | 5/2005 | Daw et al. | |
| 2006/0274928 A1 * | 12/2006 | Collins et al. | 382/132 |
| 2007/0237373 A1 | 10/2007 | Kiraly et al. | |
| 2007/0255121 A1 * | 11/2007 | Gundel | 600/300 |
| 2008/0009706 A1 * | 1/2008 | Theriault | 600/410 |

(Continued)

FOREIGN PATENT DOCUMENTS

| | | |
|---|---|---|
| JP | 2007301398 A | 11/2007 |
| WO | 2007012047 A2 | 1/2007 |
| WO | 2008072157 A2 | 6/2008 |

OTHER PUBLICATIONS

Deurloo et al ("Reduction in the number of sentinel lymph node procedures by preoperative ultrasonography of the axilla in breast cancer" European Journal of Cancer 39 (2003) 1068-1073).*

(Continued)

*Primary Examiner* — Shervin Nakhjavan

(57) ABSTRACT

A system is provided for automatic selection of medical images. The system comprises an input (302) for receiving a temporal sequence of medical images acquired with a hand-held medical imaging device. An object detector (303) is provided for detecting an object in at least one of the images. An image selector (304) is provided for selecting an image in which the object has been detected by the object detector. A snapshot means (305) is provided for storing the selected image as a snapshot. Moreover, a hand-held medical imaging device is provided for generating the sequence of medical images.

18 Claims, 5 Drawing Sheets

(56) References Cited

U.S. PATENT DOCUMENTS

| | | | |
|---|---|---|---|
| 2008/0267499 A1* | 10/2008 | Deischinger et al. | 382/173 |
| 2009/0003665 A1* | 1/2009 | Berg et al. | 382/128 |
| 2009/0054768 A1* | 2/2009 | Halmann et al. | 600/437 |
| 2009/0161926 A1* | 6/2009 | Florin et al. | 382/128 |

OTHER PUBLICATIONS

Zhu, Y., et al.; Computer technology in detection and staging of prostate carcinoma: A review; 2006; Medical Image Analysis; 10:178-199.

* cited by examiner

SELECTION OF SNAPSHOTS OF A MEDICAL IMAGE SEQUENCE

FIELD OF THE INVENTION

The invention relates to selection of a medical image. More particularly, the invention relates to a system, method, and computer program product for automatically selecting an image for storing the image as a snapshot.

BACKGROUND OF THE INVENTION

In ultrasound scans of lymph nodes or breast cancer lesions, it is common practice that the operator moves a handheld ultrasound probe and manually selects images from the resulting video stream for storing. Furthermore, the operator can optionally place graphical annotations or markers on the image in order to identify the position and extent of the structure under investigation.

Staging of axillary lymph nodes is an important step in the assessment of the spread of the disease in newly diagnosed breast cancer patients. An image-based way of pre-surgical lymph node staging consists of using ultrasound images, potentially in combination with other imaging modalities, such as MR.

The ultrasound images are acquired using a hand-held device. 2D images are selected by the operator and saved. Usually, additional markings or annotations, e.g. the long axis and the short axis of the lymph node, are placed by the operator and stored along with the images.

Also, there is a clear trend towards the use of computer-aided detection and diagnosis (CAD) systems in clinical practice. Both for the purpose of computer-aided detection and manual evaluation, the high level of operator dependence on the image acquisition of ultrasound images poses a problem.

SUMMARY OF THE INVENTION

It would be advantageous to have an improved way of selecting medical images. To better address this concern, a system is presented that comprises an input for receiving a temporal sequence of medical images acquired with a hand-held medical imaging device;

an object detector for detecting an object in at least one of the images; an image selector for selecting an image in which the object has been detected by the object detector;

a snapshot means for storing the selected image as a snapshot.

The image selector, which selects an image in which the object has been detected, helps to achieve a more operator independent selection of acquired images. In existing hand-held medical image acquisition systems, the operator manually stores snapshots of images in which the object of clinical relevance is displayed. However, this task may be automated using the object detector and image selector. Since this may decrease the operator dependence, it may increase the reproducibility of image acquisition. Also, because the operator does not have to spend time and attention on the task of selection and storage of snapshots, the image acquisition may be more efficient and/or easier for the operator. Also, in an embodiment the images that were not selected as snapshots are discarded.

An embodiment further comprises the hand-held medical imaging device for providing the sequence of medical images to the input. It is envisaged to incorporate the system set forth into a hand-held medical imaging system. For example, such a hand-held medical imaging system comprises a hand-held medical imaging device and a console. The system for selecting the images can be incorporated in the console, for example.

In an embodiment, the image selector is arranged for selecting the image while the temporal sequence is being acquired with the hand-held medical imaging device. The image selection may be performed 'on-line', during the acquisition of the images. This makes the acquisition especially efficient, since only the selected images need to be stored. Also, the operator does not need to manually select image snapshots.

An embodiment comprises an alert unit for generating an alert to an operator of the hand-held medical imaging device upon selecting the image. This way, the operator is informed about the storage of a snapshot image. It allows the operator to review the quality of the stored snapshot. If an acceptable image has been stored, the operator may stop the acquisition or continue with imaging another area of interest. Alternatively, the operator may continue the acquisition and/or store another snapshot manually or automatically.

In an embodiment, the object detector is arranged for detecting the object in a plurality of the images, therewith obtaining a set of images each comprising the object, and wherein the image selector comprises means for selecting an image from the set of images by applying a set of predetermined selection criteria representing clinical relevance of the image. The predetermined selection criteria allow the automatic image selection mechanism to refine the selection of the images. It may not be sufficient to store any random image wherein the object has been detected, but for example a particular image in which the object is shown with the greatest cross sectional area or cross sectional longitudinal axis should be stored. In view of this description, the skilled person is capable of creating selection criteria reflecting such desirable properties of objects as shown in snapshots.

An embodiment comprises means for establishing a quality value indicative of a probability that the object has been detected by the object detector or an accuracy with which the object has been detected, and wherein the image selector comprises means for selecting an image having a quality value above a predetermined threshold and/or having a maximum quality value among a plurality of quality values. Object detectors are not always completely reliable. In such a case, it is often possible to establish a value representing the probability that the object was detected or the accuracy of the object detection. If the object is being detected by fitting a particular model to the image data, a value representing the goodness of fit can be established. Such quality values can be used to select the image having a large probability/goodness of fit.

An embodiment comprises means for establishing a size of the object in an image, and wherein the image selector comprises means for selecting an image having a size above a predetermined threshold and/or having a maximum size among a plurality of sizes. The size may be measured as the longest axis, the shortest axis, the total area, or in another way. By selecting the image showing the object in a large size, it may be enforced that the cross sectional view of the object intersects the object in the middle. Alternatively, it helps to find an image showing the object in a clinically relevant way.

In an embodiment, the size represents a length of a longitudinal axis of the object. This can help, especially in elongated objects, to store an image in which the object is shown along the longest axis, which is a view of particular clinical interest.

In an embodiment, the hand-held medical imaging device comprises an ultrasound probe, the sequence of medical images comprising a sequence of 2D ultrasound images obtained from the ultrasound probe. Ultrasound is a modality typically applied in a hand-held device, and the image selection system decreases operator dependence of ultrasound snapshots. The object may, for example, comprise an axillary lymph node.

An embodiment comprises an annotator for providing annotation of the selected image, the annotation indicating or describing the object detected in the selected image by the object detector, the snapshot means comprising means for storing the annotation of the selected image. This is a useful feature for enabling a radiologist to quickly see the object which provided the reason why the image was stored. It avoids having to do the detection again at a later stage.

The annotator may comprise means for including in the annotation at least one measurement value relating to the object. This improves the usefulness of the annotation and avoids having to perform the calculations again. Examples of measurements include size and aspect ratio of the lymph node or tumor.

An embodiment comprises a method of providing automatic selection of medical images, comprising
receiving a temporal sequence of medical images acquired with a hand-held medical imaging device;
detecting an object in at least one of the images;
selecting an image in which the object has been detected by the object detector; and
storing the selected image as a snapshot.

An embodiment comprises a computer program product comprising instructions for causing a processor system to perform the method set forth.

It will be appreciated by those skilled in the art that two or more of the above-mentioned embodiments, implementations, and/or aspects of the invention may be combined in any way deemed useful.

Modifications and variations of the image acquisition apparatus, of the workstation, of the system, and/or of the computer program product, which correspond to the described modifications and variations of the system, can be carried out by a person skilled in the art on the basis of the present description.

A person skilled in the art will appreciate that the method may be applied to multidimensional image data, e.g., to 2-dimensional (2-D), 3-dimensional (3-D) or 4-dimensional (4-D) images, acquired by various acquisition modalities such as, but not limited to, standard X-ray Imaging, Computed Tomography (CT), Magnetic Resonance Imaging (MRI), Ultrasound (US), Positron Emission Tomography (PET), Single Photon Emission Computed Tomography (SPECT), and Nuclear Medicine (NM). It will also be understood that the methods and systems set forth herein may be used to advantage in conjunction with a hand-held imaging device producing a temporal sequence of 2D cross sectional images.

BRIEF DESCRIPTION OF THE DRAWINGS

These and other aspects of the invention will be further elucidated and described with reference to the drawing, in which.

DETAILED DESCRIPTION OF EMBODIMENTS

An automatic segmentation and tracking algorithm may be employed in order to segment and track lymph nodes and/or breast cancer lesions in medical images. Based on the quality of the segmentation and additional quality criteria, acquired images may be automatically selected for storing. Moreover, the selected images may automatically be labeled using the available segmentation information. An automatic segmentation and tracking algorithm may be used for segmenting the lymph node initially in a 2D ultrasound image and for tracking the lymph node in the image, while the operator moves the hand held ultrasound probe. Using image quality measures, which are based on the current segmentation result, 2D snapshots may be selected automatically for storage. The selected snap-shots may be annotated to represent the segmentation result and stored automatically by the system. This does not only reduce the workload of the operator, as there is no need for manual annotations, but at the same time assures an operator independent selection of images. This helps to obtain standardized images useful for subsequent diagnostic review or as input to a computer aided diagnosis system.

Figure 1:
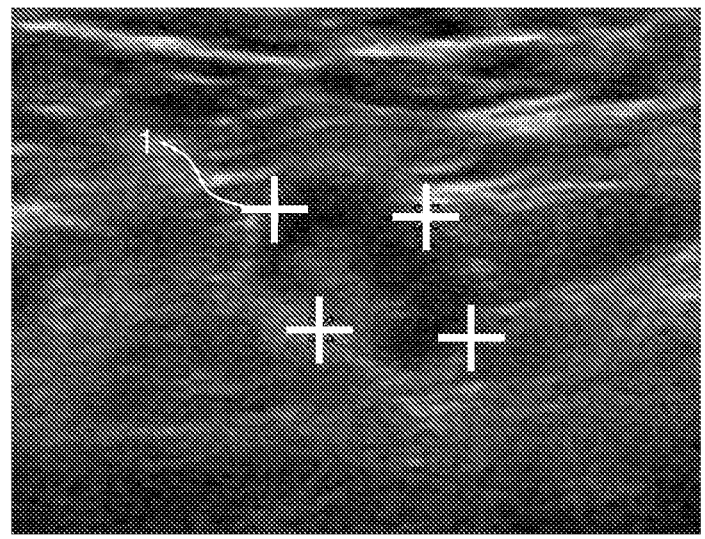
FIG. 1 illustrates an ultrasound image with a manually identified lesion.

Manual segmentation of a lymph node in a 2D ultrasound image may be by manually placing a plurality of markers on the boundary of the lymph node. FIG. 1 illustrates an axillary lymph node in an ultrasound image with manually placed markers 1 having the shape of crosshairs.

Figure 2:
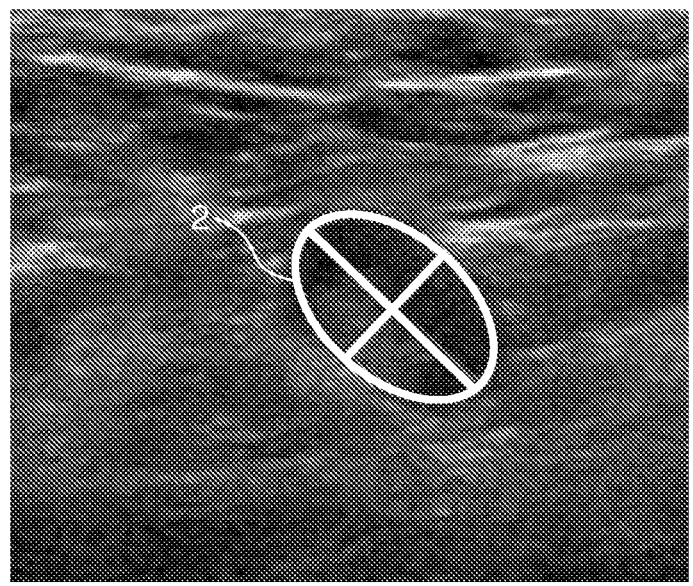
FIG. 2 illustrates an ultrasound image with an ellipse fitted to an automatically identified lesion.

One way to automatically segment a lymph node in a 2D US image is to fit an ellipse to the image data. FIG. 2 illustrates the same ultrasound image of the axillary lymph node shown in FIG. 1, with a white overlay 2 showing an automatically fitted ellipse.

Figure 3:
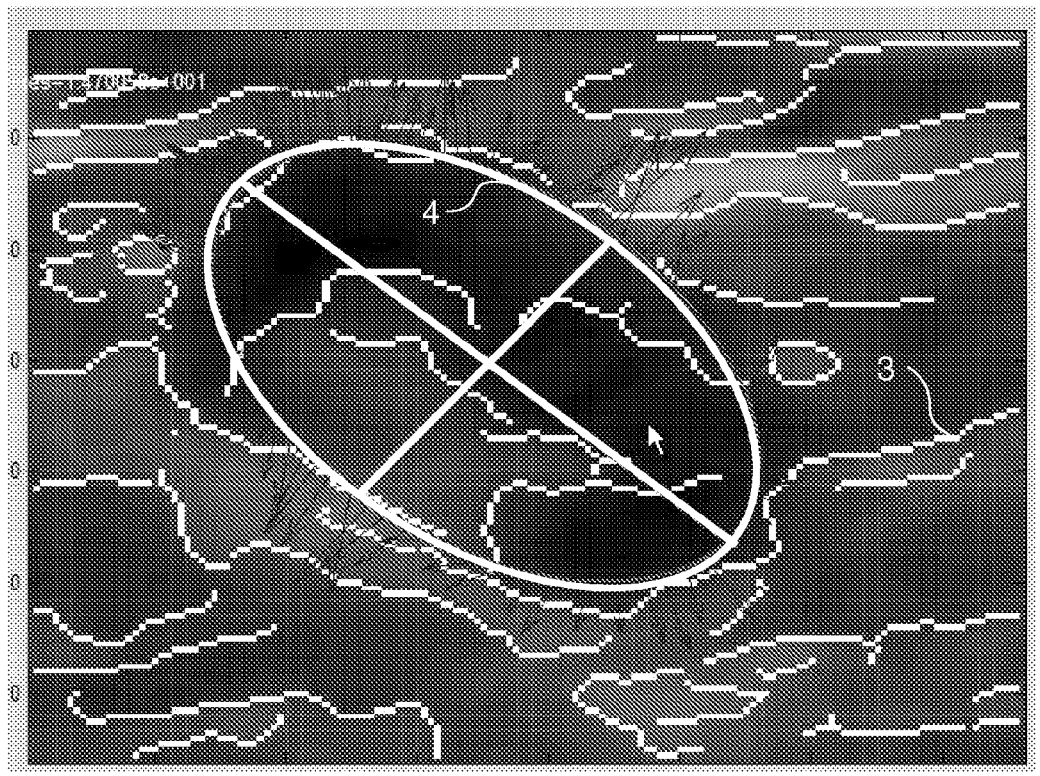
FIG. 3 illustrates an ultrasound image with high-gradient pixels and an ellipse fitted to an automatically identified lesion.

FIG. 3 illustrates diagrammatically a plurality of edge pixels 3 detected by a Canny edge detector in an ultrasound image. An ellipse fit 4 can be obtained by fitting ellipses to randomly selected sub-sets of the set of edge pixels. The goodness of the fit of each ellipse can be obtained by integrating the normal (outward-pointing) component of the image gradient vector along the ellipse boundary.

Once an initial ellipse fit to the lymph node has been obtained, the lymph node can be tracked while the ultrasound probe is moved, by searching for the best fitting ellipse in a small neighborhood of the initial ellipse. In such a way, during the ultrasound image acquisition, the ellipse parameters will be tracked.

2D snapshots may be selected automatically for storing on the basis of predefined conditions such as:

Local (in time) maxima of the goodness of the ellipse fit to the data. This goodness of fit can be established using the integration of the outward-pointing component of the image gradient vector along the ellipse boundary, for example.

Maximum extent of the lymph node (maximum long axis of the ellipse).

Maximum area of the lymph node (maximum product of long and short axis length of the ellipse).

A combination of these constraints can be applied to obtain a better selection of the stored images. For example, the goodness of fit is used in conjunction with maximum extent or maximum area. Such a combination can be obtained by multiplying the relevant parameters, in this case by multiplying a goodness of fit measure by the extent or area. The maximum value of the product may trigger the selection of an image for storage.

Other applications of the techniques set forth are possible, such as ultrasound scans of primary breast cancer lesions. Moreover, any imaging modality wherein the operator has great influence on the acquired images (which is the case in ultrasound because of the hand-held ultrasound probe which results in irreproducible viewing angles), and wherein one searches for particular image patterns, can be improved by using the automatic image selection as described herein.

The tracking of a lymph node may be visualized, for example, by superimposing graphical elements (ellipse, crosses, or similar) on the images.

Figure 4:
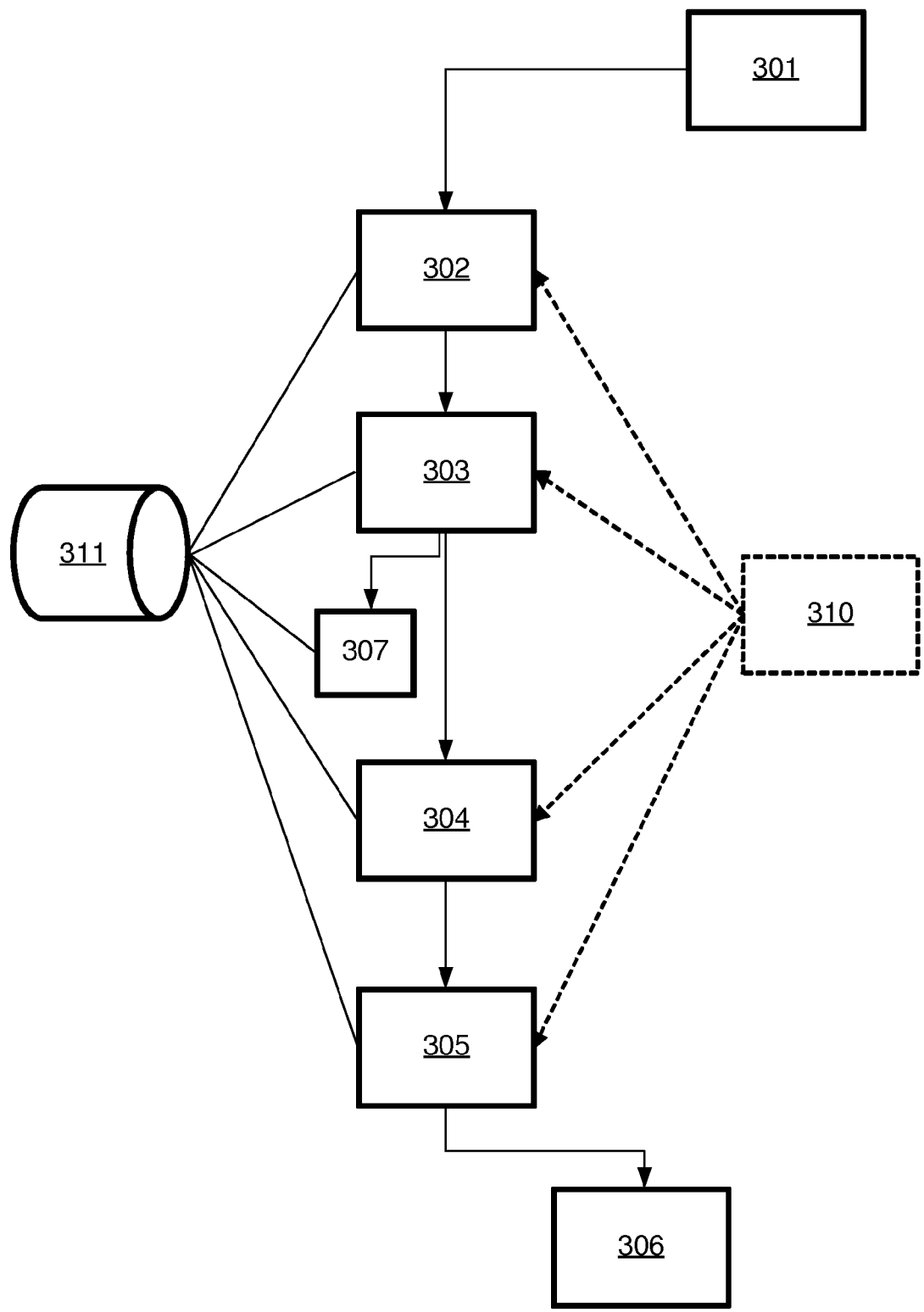
FIG. 4 illustrates a system for selecting images.

FIG. 4 illustrates a system for providing automatic selection of medical images. Such a system may comprise a processor 310 for executing computer instructions stored in a memory. The computer instructions (for example represented by blocks 302-305) are stored in a memory (not shown), such as a flash memory or a random access memory and/or a hard disk of a medical imaging console. Such a console may have more hardware parts, such as a display, a keyboard, some auxiliary buttons, a trackball or mouse, etc., for controlling the medical image acquisitions and for reviewing and annotating the acquired images. Also, a storage means 311 is provided for storing of medical images, annotations, patient information, and other information. The data may be organized in a database and the storage means 311 may comprise a random access memory, a hard disk, a flash memory, or any other storage medium including removable storage medium such as DVD or CD-ROM.

The system may comprise a hand-held image acquisition device 301. Such a hand-held image acquisition device may be employed by the operator for acquiring images of the patient. In case of an ultrasound system, the hand-held image acquisition device comprises an ultrasound probe. The operator typically prepares a portion of the skin of the patient at the place where the images have to be acquired. After that, the operator places the ultrasound probe on the skin and moves and rotates the probe while acquiring images, in order to find good views of an object of interest, for example a lesion or a lymph nodule.

During acquisition, a series of images is transmitted from the hand-held imaging device 301 to an input 302, which receives the images from the hand-held medical imaging device 301 and temporally stores the images in the storage means 311, for example in the random access memory thereof.

Object detector 303 is arranged for detecting an object in at least one of the images. To that effect, the object detector analyzes the images received via the input 302 for the presence of objects. This may be performed by fitting of an ellipse to high-gradient pixels, as set forth above. However, other suitable methods and systems for object detection will be apparent to the skilled person in view of this description. The object detector may outline the extent of the object in the image, for example by fitting of the ellipse. Alternatively, the object detector may simply detect the presence of the object in the image. Object parameters such as location in the image and/or object boundary may be temporarily stored in the storage means 311.

Image selector 304 selects an image in which the object has been detected by the object detector. To this end, it receives from the object detector 303 information about in which image or images the object has been detected. Depending on the application at hand, the image selector may store snapshots of all images in which an object has been detected, or it may select (a) particular image(s) in which an object has been detected. For example, the object detector may be capable of indicating whether the same object or a different object is detected in different images; the image selector may then be arranged for storing one snapshot of every object detected. The information about detected objects may be done via the storage means 311.

Snapshot means 305 stores the selected image or images as a snapshot or snapshots. These snapshots may be included in a patient file automatically. They may also be included in a report. The images temporarily stored in the storage means 311 may be deleted after having selected and stored the snapshot images. Alternatively, the complete series of images is stored permanently and the selected images are labeled as snapshots. The annotations, if any, produced by the object detector may be stored separately or as graphical drawings within the image.

In a typical operating mode of the system set forth, the object detector detects the objects in the images as soon as they have been transmitted from the hand-held device 301 to the input 302. The image selector is arranged for selecting the image while the temporal sequence is being acquired with the hand-held medical imaging device. In this operating mode, the images are selected 'on-the-fly', or in 'real-time'. It saves storage space, since as soon as the image selection process has been performed the images which have not been selected may be deleted from the system. Also, as soon as suitable images have been selected, the acquisition may stop, which saves time.

An embodiment comprises an alert unit 306 for generating an alert to an operator of the hand-held medical imaging device upon selecting the image. This is an effective way of notifying the operator that a suitable image has been stored, so the operator can stop or proceed to the next lesion or object of interest. The alert may comprise an audible signal, for example a beep, and/or a visible signal, for example a popup window on the console or a light signal produced by a lamp in the hand-held device.

It is possible to define selection criteria which can be applied to detected objects to establish a measure of the clinical relevance thereof In an embodiment, the image selector comprises means for selecting an image among a plurality of images in which the object detector has selected an object by applying a set of such predetermined selection criteria representing clinical relevance of the image. Such criteria may relate to the size, shape, grey levels, texture, or location of the object, for example. In case the object detection comprises an ellipse fit, possible exemplary criteria include area of the ellipse, longest axis of the ellipse, and ratio of longest and shortest axis of the ellipse. Such values may be compared to a threshold; the image is only stored if the threshold is exceeded, for example.

Alternatively, values characterizing the clinical relevance may be computed for a sequence of images comprising the object, and the image having the most favorable value may be selected and stored as a snapshot. The most favorable value may be the highest value, for example, or the lowest, depending on how the values were computed, as the skilled person will understand.

An embodiment comprises means for establishing a quality value indicative of an accuracy with which the object has been detected by the object detector. Such a quality value is indicative of the clinical relevance of the image, because if the object has been poorly detected, there might not be any object in the image, or any estimated properties of the object such as the size, could be wrong. A selection criterion is applied favoring an image having a quality value above a predetermined threshold and/or having a maximum quality value among a plurality of quality values. This way, images are stored for which the object detection was successful.

An embodiment comprises means for establishing a size of the object in an image. In this embodiment, a selection criterion is applied for selecting an image having a size above a predetermined threshold and/or having a maximum size among a plurality of sizes. If the size is largest, it is reasonable to assume that the object is best visible and in greatest detail. In particular in the case of 2D images, such as 2D ultrasound images, which constitute a cross section of the object being imaged, if the object is largest, this means that the cross section intersects a large portion of the object, which provides the most clinical information, in particular about the real size of the object in 3D. The size may be a length of a longitudinal axis of the object. In this case, orientations of the probe in which the full length of the object is imaged are selected.

The object may comprise an axillary lymph node. The procedure of imaging such lymph nodes can be made more efficient. The results of the procedure can be made more operator independent by applying the image selector for selecting snapshots.

An embodiment comprises an annotator 307 for providing annotation of the selected image. This annotation is generated based on the object detected by the object detector 303. The annotation represents the object detected in the selected image. For example, the annotation comprises a graphical object indicating a boundary of the detected object. Also, the annotation may comprise numerical information of the detected object such as its size. Patient information may also be included in the annotation.

Figure 5:
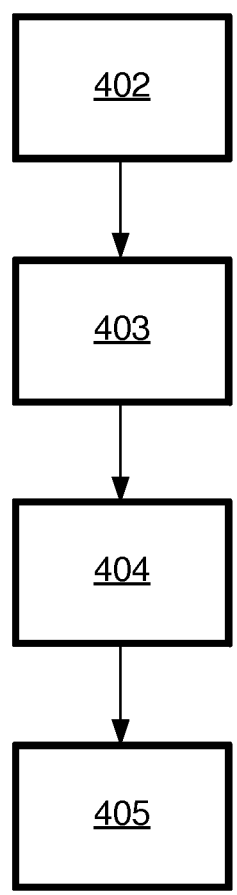
FIG. 5 illustrates a method of selecting images.

FIG. 5 illustrates processing steps of a method of providing automatic selection of medical images. In step 402, a temporal sequence is received, the sequence comprising medical images acquired with a hand-held medical imaging modality. In step 403, an object is detected in at least one of the images. In step 404, an image is selected in which the object has been detected by the object detector. In step 405, the selected image is stored as a snapshot. The method may be started by a button pressed by the operator which indicates the acquisition of a new image series. The method may be finished by the end of the image sequence. In a real-time mode, images may be temporarily stored in a buffer in storage means 311. The image detector 303 may be applied to each image sequentially. The image selector may compute a value representing the suitability of each image as a snapshot, using some of the selection criteria outlined above. In this way, a temporal sequence of suitability values is obtained corresponding to the temporal image sequence. In this temporal sequence of suitability values, a local maximum may be found using maximum detectors known in the art as such. The image selector 304 may be arranged to detect such a local maximum of a suitability value. The image selector 304 may further be arranged to select the image corresponding to the local maximum of the suitability value for storage as a snapshot.

Figure 6:
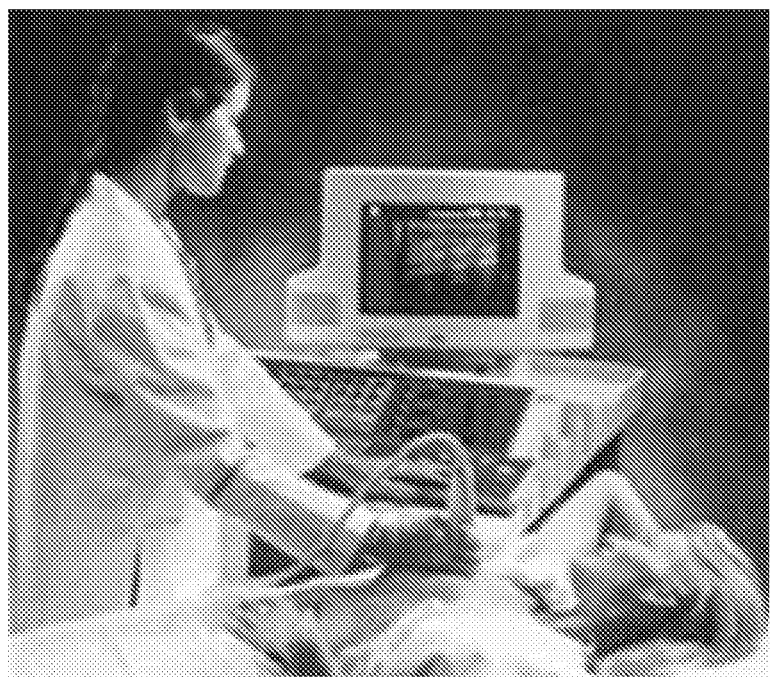
FIG. 6 illustrates a medical examination using a hand-held imaging device.

FIG. 6 illustrates a medical examination using a hand-held device. The image shows a patient lying down, an operator holding a hand-held imaging device, and, in the background, a console for displaying images obtained using the hand-held imaging device.

Although in the description, the focus has been on breast lesions, it will be appreciated that the embodiments described herein can also be applied to other medical imaging applications. For example, the techniques set forth herein can be used when investigating other objects within the body using a handheld medical imaging device. A particular example hereof is liver cancer investigation.

It will be appreciated that the invention also extends to computer programs, particularly computer programs on or in a carrier, adapted for putting the invention into practice. The program may be in the form of source code, object code, a code intermediate source and object code such as partially compiled form, or in any other form suitable for use in the implementation of the method according to the invention. It will also be appreciated that such a program may have many different architectural designs. For example, a program code implementing the functionality of the method or system according to the invention may be subdivided into one or more subroutines. Many different ways to distribute the functionality among these subroutines will be apparent to the skilled person. The subroutines may be stored together in one executable file to form a self-contained program. Such an executable file may comprise computer executable instructions, for example processor instructions and/or interpreter instructions (e.g. Java interpreter instructions). Alternatively, one or more or all of the subroutines may be stored in at least one external library file and linked with a main program either statically or dynamically, e.g. at run-time. The main program contains at least one call to at least one of the subroutines. Also, the subroutines may comprise function calls to each other. An embodiment relating to a computer program product comprises computer executable instructions corresponding to each of the processing steps of at least one of the methods set forth. These instructions may be subdivided into subroutines and/or be stored in one or more files that may be linked statically or dynamically. Another embodiment relating to a computer program product comprises computer executable instructions corresponding to each of the means of at least one of the systems and/or products set forth. These instructions may be subdivided into subroutines and/or be stored in one or more files that may be linked statically or dynamically.

The carrier of a computer program may be any entity or device capable of carrying the program. For example, the carrier may include a storage medium, such as a ROM, for example a CD ROM or a semiconductor ROM, or a magnetic recording medium, for example a floppy disc or hard disk. Further, the carrier may be a transmissible carrier such as an electrical or optical signal, which may be conveyed via electrical or optical cable or by radio or other means. When the program is embodied in such a signal, the carrier may be constituted by such a cable or other device or means. Alternatively, the carrier may be an integrated circuit in which the program is embedded, the integrated circuit being adapted for performing, or for use in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for providing automatic selection of medical images, comprising:
   a hand-held medical imaging device for providing a temporal sequence of medical images; and
   one or more processors programmed to:
      receive the temporal sequence of medical images acquired with the hand-held medical imaging device;
      detect an object in at least one of the images by segmenting the image to produce an image segmentation;
      automatically select an image while the temporal sequence is being acquired with the hand-held medical imaging device, the selected image being an image in which the object has been detected by the object detector by calculating selection values based on the image segmentation;
      control an alert unit generate an alert to an operator of the hand-held medical imaging device upon selecting the image; and
      a storage medium which stores the selected image as a snapshot.

2. The system as claimed in claim 1, wherein the one or more processors are further programmed to:
   detect the object in the temporal sequence of images, therewith obtaining a set of images each comprising the object; and
   select an image from the set of images by applying a set of predetermined selection criteria to the selection values, the selection criteria including criteria representing clinical relevance of the image.

3. The system as claimed in claim 2, wherein the one or more processors are further programmed to:
   calculate a quality value indicative of an accuracy with which the object has been detected by the object detector, the predetermined selection criteria including at least one criterion for selecting an image having a quality value above a predetermined threshold and/or having a maximum quality value among a plurality of quality values.

4. The system as claimed in claim 2, wherein the one or more processors are further programmed to:
   establish a size of the object in an image based on the calculated selection values, the predetermined selection criteria including at least one criterion for selecting an image having a size above a predetermined threshold and/or having a maximum size among a plurality of sizes.

5. The system as claimed in claim 4, wherein the size represents a length of a longitudinal axis of the object.

6. The system of claim 2, wherein the object is segmented by fitting a model, the selection values include, goodness of the model fit, and the selection criteria include identifying a local temporal maxima of the goodness of fit.

7. The system of claim 2, wherein the object is segmented by fitting an ellipse and the selection values include a size of the detected object.

8. The system of claim 7, wherein the selection criteria include identifying local temporal maxima of the size of the detected object.

9. The system of claim 7, wherein the selection criteria include a minimum threshold of the size of the detected object.

10. The system of claim 2, wherein the selection values include an area of the detected object.

11. The system of claim 10, wherein the selection criteria include a threshold for at least one of a maximum and a minimum of the area of the detected object.

12. The system as claimed in claim 1, wherein the hand-held medical imaging device comprises an ultrasound probe, the sequence of medical images comprising a sequence of 2D ultrasound images obtained from the ultrasound probe.

13. The system as claimed in claim 1, wherein the object includes an axillary lymph node.

14. The system as claimed in claim 1, wherein the one or more processors are further programmed to:
   annotate the selected image with an annotation indicating or describing the object detected in the selected image by the object detector, the storage medium storing the annotation of the selected image.

15. The system as claimed in claim 14, wherein the annotation includes at least one measurement value relating to the object.

16. A system for automatically selecting medical images comprising:
   a hand-held medical imaging device for providing a real-time sequence of medical images; and
      receive the real-time sequence of medical images;
      analyze the sequence of images to detect an object of interest in a plurality of the received images to identify a set of the received images which include the object,
      apply a predeterminded selection criteria indicative of clinical relevance to the set of images to select one or more images of the set, the selection criteria including one or more of size, shape, grey levels, texture, and location of the object, and including a quality value indicative of an accuracy with which the object has been selected,
      determine an annotation including at least one physical measurement of the object in the selected one or more images;
      generate an alert to an operator to accept the selected images of the set; and
   a memory in which the selected images and associated annotations are stored in response to receiving operator acceptance of the selected images.

17. A method of providing automatic selection of medical images, comprising:
   with one or more processors, receiving a temporal sequence of medical images acquired with a hand-held medical imaging device;
   with the one or more processors, detecting an object in at least one of the images by segmenting the image;
   with the one or more processors, selecting an image in which the object has been detected by the object detector by calculating selection values based on the image segmentation and applying selection criteria to the selection values, the selection values including goodness of fit data; and
   in a memory, storing the selected image as a snapshot.

18. A non-transitory computer program product comprising instructions for causing a processor system to perform the method as claimed in claim 17.

* * * * *